United States Patent
Bell et al.

(10) Patent No.: US 6,172,117 B1
(45) Date of Patent: Jan. 9, 2001

(54) BIOCIDAL PRESERVATIVES

(75) Inventors: John P. Bell, Ossining; Andress K. Doyle, Pleasantville, both of NY (US); Robert F. Farmer, Barrington, IL (US); James F. Gadberyy, Danbury, CT (US); Douglas Lucas, Garden City Park, NY (US); Stanley B. Mirviss, Stamford, CT (US); William Parr, Holten (NL)

(73) Assignee: Akzo Nobel N.V. (NL)

( * ) Notice: Under 35 U.S.C. 154(b), the term of this patent shall be extended for 0 days.

(21) Appl. No.: 09/032,604

(22) Filed: Feb. 27, 1998

(51) Int. Cl.$^7$ .......................... A01N 25/00; A01N 47/00; A01N 33/12; A01N 43/40; A01N 43/36

(52) U.S. Cl. .......................... 514/642; 514/514; 514/642; 514/643; 514/515; 514/315; 514/358; 514/428; 514/183; 514/210; 514/212; 424/405

(58) Field of Search ..................................... 514/642, 643, 514/514, 315, 358, 428, 183, 210, 212; 424/405

(56) References Cited

U.S. PATENT DOCUMENTS

| | | | |
|---|---|---|---|
| 2,214,971 | * 9/1940 | Muller et al. | 260/454 |
| 2,876,217 | 3/1959 | Paschall | 260/233.3 |
| 3,681,377 | 8/1972 | Singhal | 260/309.5 |
| 3,738,945 | 6/1973 | Panzer et al. | 260/2 |
| 3,943,255 | 3/1976 | Newkirk | 424/329 |
| 4,018,592 | 4/1977 | Buckman et al. | 71/67 |
| 4,111,679 | 9/1978 | Shair et al. | 71/67 |
| 4,140,798 | 2/1979 | Merianos et al. | 424/325 |
| 4,325,940 | 4/1982 | Green et al. | 427/70 |
| 4,506,081 | 3/1985 | Fenyes et al. | 548/523 |
| 4,581,058 | 4/1986 | Fenyes et al. | 71/67 |
| 4,883,917 | 11/1989 | Smith et al. | 106/18.33 |
| 4,982,000 | 1/1991 | Earl et al. | 564/290 |
| 5,051,124 | 9/1991 | Pera | 71/67 |
| 5,078,912 | 1/1992 | Goettsche et al. | 252/400.53 |
| 5,139,791 | 8/1992 | Nakajima et al. | 426/2 |
| 5,288,866 | 2/1994 | Strong | 544/215 |
| 5,304,237 | 4/1994 | Barth et al. | 106/18.3 |
| 5,354,565 | 10/1994 | Iwasaki et al. | 424/605 |
| 5,378,843 | 1/1995 | Strong | 544/215 |
| 5,426,121 | 6/1995 | Bell . | |
| 5,438,034 | 8/1995 | Walker | 504/158 |
| 5,536,305 | 7/1996 | Yu | 106/18.33 |
| 5,730,907 | * 3/1998 | Schultz et al. | 252/400.62 |

FOREIGN PATENT DOCUMENTS

| | | |
|---|---|---|
| 32 35 639 | 4/1983 | (DE) . |
| 3520394 | 12/1986 | (DE) . |
| 238051 | 9/1987 | (EP) . |
| 238413 | 9/1987 | (EP) . |
| 370182 | 5/1990 | (EP) . |
| 549006 | 6/1993 | (EP) . |
| 556454 | 8/1993 | (EP) . |
| 509346 | 3/1997 | (EP) . |
| 9081535 | 8/1974 | (JP) . |
| 1006927 | 1/1976 | (JP) . |
| 1102001 | 4/1989 | (JP) . |
| 1102002 | 4/1989 | (JP) . |
| 1203304 | 8/1989 | (JP) . |
| 1204701 | 8/1989 | (JP) . |
| 1233264 | 9/1989 | (JP) . |
| 2045460 | 2/1990 | (JP) . |
| 2115105 | 4/1990 | (JP) . |
| 2311405 | 12/1990 | (JP) . |
| 4005206 | 1/1992 | (JP) . |
| 7291923 | 7/1995 | (JP) . |
| 8188503 | 7/1996 | (JP) . |
| WO 82 03817 | 11/1982 | (WO) . |
| WO 9428715 | 12/1994 | (WO) . |
| WO 97 45236 | 12/1997 | (WO) . |

OTHER PUBLICATIONS

Butcher et al., "Intial Screening Trials of Some Quaternary Ammonium Compounds and Amine Salts as Wood Preservatives", Forest Products Journal, (1977), vol. 27, No. 7, pp. 19–22.

Cox et al., "Sterility testing: detection of fungi and yeasts in the presence of preservatives", Journal of Biological Standardization, (1973) 1, pp. 11–19.

DaCosta et al., "Potential Toxicants for Controlling Soft Rot in Preservative Treated Hardwoods", Mater. Org.; 14(2), (1979), pp. 131–140.

Kim et al., "Preparation of bis–Quaternary Ammonium Salts from Epichlorohydrin", JAOCS, vol. 73, No. 1 (1996), pp. 67–71.

PCT INT'L Search Report PCT/EP99/01306.

Derwent Abstract 88–237301, 3/23/88.

Derwent Abstract 94–188855, 5/10/94.

Mirakhmedov et al.(CA 100:175096, abstract of Uzb. Khim. Zh. (1983), (5), 53–56.*

CA, Beilstein RN (BRN) 3715901.*

* cited by examiner

*Primary Examiner*—Sabiha N. Qazi
(74) *Attorney, Agent, or Firm*—Dilworth & Barrese

(57) ABSTRACT

Biocidal preservatives for use especially in preventing rotting and deterioration of wood include quaternary ammonium compounds which preferably have a fatty aliphatic substituent on the quaternary nitrogen atom. Especially preferred are cocoalkyl substituents. Other substituents can include alkoxy groups, arenes, and heterocyclic groups with or without ring substitutions, for example. The quaternary ammonium compound can also contain an amine nitrogen and can be complexed with copper.

9 Claims, No Drawings

BIOCIDAL PRESERVATIVES

BACKGROUND

1. Technical Field

This disclosure relates to preservatives, and particularly to biocidal preservative agents suitable for the preservation of wood, cotton, and other materials.

2. Background of the Art

Biocidal agents are often used to prevent the rotting and deterioration of various materials caused by bacteria, algae, fungus and mold. Such agents are especially needed for the preservation of wood, which is commonly used as a construction material.

Various formulations are available for the preservation of wood. Inorganic salts, particularly chromated copper arsenate, have often been used to treat wood. However, such salts pose a problem with respect to ground contamination as they leach from the wood.

As an alternative to the use of inorganic salts, organic compounds, optionally complexed with an inorganic metal such as copper, have also been used.

For example, U.S. Pat. No. 5,426,121 to Bell discloses wood preservatives which comprise a solution of a complex derived from copper and an alkoxylated diamine containing at least one fatty alkyl group.

U.S. Pat. No. 5,536,305 to Yu discloses a wood preservative composition consisting essentially of 4,5-dichloro-2-n-3-isothiazolone and a surfactant such as an anionic, cationic, or amphoteric surfactant.

Quaternary ammonium compounds are also known to be useful biocidal agents. However, wood treated with quaternary ammonium compounds tends to fail when used in applications with high decay hazards, such as in ground uses like posts, pilings and utility poles. Accordingly, it is desirable to develop quaternary ammonium compounds that may have greater biocidal activity.

SUMMARY OF THE INVENTION

Biocidal preservative compositions are provided herein. The preservative compositions comprise one or more compounds of the following formulas (I)–(III).

Thus, in one embodiment the preservative composition comprises a compound of the formula:

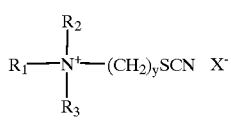

(I)

wherein $X^-$ is an anion and y can vary from 1 to 12, and $R_1$, $R_2$ and $R_3$ can be the same or different and are independently selected from the group consisting of straight or branched chain aliphatic moieties of from about 1 to about 22 carbon atoms, benzyl moieties with or without substitutions, —$(C_aH_{2a}O)_nH$ wherein a is 2, 3, or 4 and n is from about 1 to about 20 and 2-hydroxyl-2-phenylethyl. Optionally, $R_1$ and $R_2$ with $N^+$ can form a heterocyclic moiety having from about 4 to about 10 carbon atoms.

In yet another embodiment the preservative composition comprises a compound of the formula:

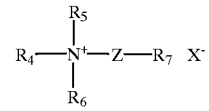

(II)

wherein $X^-$ is an anion, $R_4$ is a straight or branched chain aliphatic moiety having from about 6 to about 22 carbon atoms; $R_5$ and $R_6$ can be the same or different and are independently selected from the group consisting of aliphatic moieties of from about 1 to about 22 carbon atoms, —$(C_aH_{2a}O)_nH$ wherein a is 2, 3, or 4 and n is from about 1 to about 20 and 2-hydroxyl-2-phenylethyl; Z is a bridging group of the formula —$(C_aH_{2a}O)_n$—$CHY)_x$— wherein a is from about 1 to about 4, n is from 0 to about 10, x is from about 1 to about 10 and Y is the same or different at each occurrence and is selected from the group consisting of hydrogen and hydroxyl groups; and $R_7$ is chosen from the group consisting of amine groups having the formula —$NR_8R_9$ and sulfur moieties having the formula —$SR_{10}$ wherein $R_8$ and $R_9$ are individually an aliphatic moiety of from about 1 to about 22 carbon atoms, —$(C_aH_{2a}O)_nH$ wherein a is 2, 3, or 4 and n is from about 1 to about 20 or 2-hydroxyl-2-phenylethyl, $R_8$ and $R_9$ with N optionally forming a heterocyclic moiety having from about 2 to about 8 carbon atoms and $R_{10}$ is selected from the group consisting of straight or branched chain aliphatic moieties having from 1 to about 22 carbon atoms, phenyl and a heterocyclic moieties containing N, S or O and having from about 2 to about 8 carbon atoms in the ring. Compositions containing compounds of the general formula (II) can also contain copper ions to enhance performance.

In yet another embodiment the preservative composition comprises a compound having the formula:

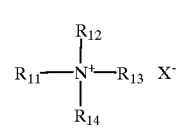

(III)

wherein $X^-$ is an anion; $R_{11}$, $R_{12}$, $R_{13}$ can be the same or different and are selected from the group consisting of $R_{14}$, straight or branched chain aliphatic moieties of from 1 to about 22 carbon atoms, and benzyl moieties optionally having one or more ring substituent selected from the group consisting of chloro, methyl, ethyl, propyl, bromo, iodo, fluoro, trifluoromethyl, hydroxy, methoxy and phenyl; $R_{14}$ is —$(CH_2$—$CHR_{15}$—$O)_xR_{16}$ wherein x is 1 to 20, $R_{15}$ is hydrogen, methyl, ethyl or phenyl, and $R_{16}$ selected from the group consisting of benzyl, napthobenzyl and picoyl moieties optionally having one or more ring substituent selected from the group consisting of chloro, methyl, ethyl, propyl, bromo, iodo, fluoro, trifluoromethyl, hydroxy, methoxy and phenyl, or $R_{16}$ is —$(CH_2)_yR_{17}$ wherein y is from 1 to about 5 and $R_{17}$ is a moiety selected from the group consisting of nitrogen-containing heterocyclic groups having 5 to 8 members in the ring, such as, for example morpholin-4-yl, piperidin-1-yl and pyrrolidin-1-yl groups.

DETAILED DESCRIPTION OF PREFERRED EMBODIMENT(S)

The preservatives described herein are compositions having a biocidal effect on microorganisms such as bacteria, algae, mold and fungus, thereby preventing rotting and deterioration. While these compositions are particularly adapted for use as preservatives for wood, they are also generally useful in applications where biocides are needed such as preservatives for cotton, and for metalworking fluids, recirculating water systems, cooling water systems, and swimming pools, for example.

In one embodiment the biocidal preservative composition includes a compound of formula (II):

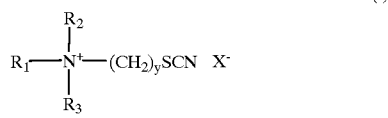

(I)

wherein $X^-$ is an anion such as, but not limited to, chloride, fluoride, bromide, iodide, acetate, methylsulfate, formate, carbonate, methylcarbonate, nitrate, nitrite, hydroxide, borate, tetraborate, perchlorate, periodate, and phosphate. Preferably, $X^-$ is a halide, most preferably chloride.

The value of y in the general formula I can vary from 1 to about 12. Preferably, y is from 1 to about 3. Most preferably, y=1.

$R_1$, $R_2$, and $R_3$ can be the same or different and are independently selected from a straight or branched chain aliphatic moiety of from about 1 to about 22 carbon atoms, a benzyl moiety with or without substituents, $-(C_aH_{2a}O)_nH$ wherein a is 2, 3, or 4 and n is from about 1 to about 20, 2-hydroxyl-2-phenylethyl. Optionally, $R_1$ and $R_2$ with $N^+$ can form a heterocyclic moiety having from about 4 to about 10 carbon atoms, such as a pyrrole, piperidine or morpholine ring.

Preferably, at least one of $R_1$, $R_2$ and $R_3$ should be a saturated or unsaturated, straight or branched chain aliphatic moiety of from about 1 to about 22 carbon atoms, more preferably from about 6 to about 22 carbon atoms, most preferably 10 to 18 carbon atoms. The aliphatic moiety may have a fixed chain length or may be of mixed chain length such as those groups derived from natural fats or oils or petroleum stocks. Preferably, the aliphatic moiety is a fatty aliphatic such as tallow alkyl, rapeseed alkyl, oleyl, cocoalkyl, soya alkyl and the like. Most preferred is cocoalkyl. In particularly useful embodiment, $R_1$ is a $C_{10}$ to $C_{18}$ aliphatic moiety and $R_2$ and $R_3$ are independently selected from $C_1$ to $C_3$ alkyl moieties, most preferably —$CH_3$. Thus, preferred compounds of formula (I) include dimethylcocoalkyl(thiocyanatomethyl) ammonium chlorides and dimethyldodecyl(thiocyanatomethyl)ammonium chloride.

Compounds of formula (I) can be made in accordance with the following procedure:

A haloalkyl thiocyanate is reacted with an amine compound having the formula

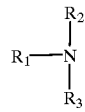

wherein $R_1$, $R_2$ and $R_3$ are as specified above, to produce a compound of formula (I).

In a preferred embodiment, the haloalkyl thiocyanate is prepared by reacting a compound of the formula $X(CH_2)_yBr$ wherein y is from 1 to about 12, X is a halogen with an inorganic thiocyanate salt of the formula MSCN where M is a cation selected from the group consisting of $Na^+$, $K^+$ and $NH_4^+$.

EXAMPLE 1

Preparation of Dimethyldodecyl(thiocyanatomethyl) ammonium Chloride

A 2 liter flask was charged with 1 liter of tetrahydrofuran, 277 g of dimethyldodecylamine and then 153.7 g of chloromethylthiocyanate. The reaction mixture was stirred at ambient temperature for 17 hours. A considerable amount of solids was formed. The reaction was then stirred for 7 more hours at 35° C. The solid was filtered off with suction and the solid washed with diethyl ether. The filtrate now formed more solid which was filtered off, washed with ether and then combined with the other solid. The combined solids were now allowed to air dry to constant weight, 331.0 g, for a 79.4% yield. Analysis (nmr) showed a purity of better than 98%.

EXAMPLE 2

Preparation of Dimethylcocoalkyl (thiocyanatomethyl)ammonium Chlorides

A 250 ml flask was charged with 125 ml. of tetrahydrofuran, 22.2 g. of dimethylcocoalkylamines (available from Akzo Nobel Chemicals of Chicago, Ill. under the designation of Armeen® DMCD) and then, with stirring, 11.5 g. of chloromethylthiocyanate. The reaction mixture was stirred overnight at the ambient (15 hrs.) and then 8 hrs. at 35° C. Some solid was present. The entire reaction mixture was now rotary evaporator stripped with aspirator vacuum with a final temperature of 69° C. at 18 torr. The solid residue had weight 34.2 g. Analysis by nmr showed a purity of 89 wt. % and a titration analysis a purity of 91.5 wt. %.

EXAMPLE 3

Preparation of Dicocoalkylmethyl (thiocyanatomethyl)ammonium Chlorides

The reaction was carried out as in Examples 1 and 2 using 125 ml. of tetrahydrofuran, 36.7 g. of dicocoalkylmethylamines (available from Akzo Nobel Chemicals of Chicago, Ill. under the designation of Armeen M2C), 11.5 g. of chloromethylthiocyanate and 0.5 g. of lithium bromide. The reaction mixture was rotary evaporator stripped to a final condition of 70° C. at 19 torr. The residue, a waxy solid, had weight 49.7 g. Titration analysis showed a purity of 95 wt. % and nmr a purity of 81 wt. %. The remainder was essentially only unreacted amine (5% by titration and 16% by nmr).

EXAMPLE 4

Preparation of Dimethyltetradecyl (thiocyanatomethyl)ammonium Chloride

The reaction was carried out similar to the other examples, using tetrahydrofuran, tetradecyldimethylamine and chloromethylthiocyanate. The product was a brown solid with 80% purity.

EXAMPLE 5

Preparation of Dimethyldecyl(thiocyanatomethyl) ammonium Chloride

The reaction was carried out similar to the other examples using tetrahydrofuran, docyldimethylamine and chloromethylthiocyanate. The solid product isolated by filtration after air drying was formed in 95% yield with essentially a 100% purity by nmr.

Compounds were evaluated for fungicidal activity by standard petri plate screening with pure cultures of *C. puteana*. The procedure was as follows:

Solutions of 4% malt agar were made up and sterilized. Once cooled a sterilized stock solution of a test compound was added to give a concentration of 1,000 ppm in the malt media. The media was then added to petri plates. For each plate, approximately 10 mls of agar were poured and allowed to solidify. Then 6 mm cores of the inoculum (*C. puteana*) were transferred from culture plates to the center of each test plate. Four replicates for the control (agar only) and for each of the test compounds—treated plates were then inoculated. The plates were incubated at 25° C. for a minimum of two weeks. The diameter of fungal growth present on each plate was measured daily over this period. Growth curves for the fungi were developed and the growth rate on the linear portion was determined.

The growth rate data is given in Table I in terms of a 0 to 10 scale defined as growth inhibition. If there is no growth of a fungus on plate, then the growth inhibition is 10. In the cases where there is growth, a % inhibition value is first calculated, where:

% inhibition=$(1-(G_c/G_{nc}))*100$ where:

$G_c$=Growth rate with chemical $G_{nc}$=Growth rate with no chemical

Then 0 to 9.9% inhibition is defined as 0, 10.0% to 19.9% as 1, etc. The results for the testing is shown in Table I.

TABLE I

| Compound | Growth Inhibition C. puteana |
|---|---|
| Dimethyldecyl(thiocyanomethyl)ammonium chloride | 10 |
| Dimethyldodecyl(thiocyanomethyl)ammonium chloride | 10 |
| Dimethyltetradecyl(thiocyanomethyl)ammonium chloride | 9 |
| Dimethylcocoalkyl(thiocyanomethyl)ammonium chlorides | 10 |
| Dicocoalkylmethyl(thiocyanomethyl)ammonium chlorides | 10 |
| Trimethylcocoalkylammonium chlorides (Comparative Std.) | 9 |

EXAMPLE 6

A comparison was made between the biocidal effectiveness of dimethyldodecyl(thiocyanatomethyl)ammonium chloride ("TCQ-12") and trimethyldodecylammonium chloride which is available under the designation Arquad 12W-35 from Akzo Nobel Chemicals, Inc., Chicago, Ill.

Testing was performed in accordance with CEN standards prEN 1276 for bactericidal activity and prEN 1650 for fungicidal activity. Test organisms were *Pseudomonas aeruginosa* and *Staphylococcus aureus* as bacteria and *Candida albicans* as fungus. Test conditions were 0.03% bovine serum albumin as protein load (clean conditions), 20° C. and a water hardness of 300 mg/kg as $CaCO_3$ (17° dH). The test results are set forth in Table III, below. The contact times in the table are those that give the required log 5 reduction for bacteria and the log 4 reduction for fungi at a given biocide concentration. The required maximum time to pass the test was 5 minutes for bacteria and 15 minutes for fungi.

TABLE II

| | TCQ-12 | | Arquad 12W-35 | |
|---|---|---|---|---|
| Test organism | concentration [ppm a.s.] | contact time [min] | concentration [ppm a.s.] | contact time [min] |
| *Pseudomonas aeruginosa* | 500 | 15 | 2200 | >15 |
| | 600 | 5 | 2400 | 5 |
| | 700 | 1 | 2600 | 5 |
| *Staphylococcus aureus* | 70 | 15 | 200 | >5 |
| | 100 | 5 | 300 | 5 |
| | 300 | 5 | 380 | 5 |
| *Candida albicans* | 650 | 15–30 | 1600 | 30 |
| | 750 | 15 | 2200 | 15 |
| | 1000 | 5 | 2600 | 5 |

As can be seen from this example, the incorporation of the thiocyanatomethyl group into the structure of the ARQUAD 12W-35 results in a 3 to 4 times increase in the effectiveness of the compound against the tested organisms.

In another embodiment the biocidal preservative composition includes a compound of formula (II):

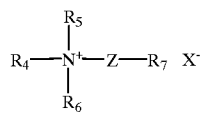

(II)

wherein $X^-$ is an anion such as, but not limited to, chloride, fluoride, bromide, iodide, acetate, methylsulfate, formate, carbonate, methylcarbonate, nitrate, nitrite, hydroxide, borate, tetraborate, perchlorate, periodate, and phosphate. Preferably, $X^-$ is a halide, most preferably chloride.

$R_4$ is a straight or branched chain aliphatic moiety having from about 6 to about 22 carbon atoms, preferably 10 to 20 carbon atoms, most preferably 12 to 18 carbon atoms. $R_4$ may have a fixed chain length or may be of mixed chain length such as those groups derived from natural fats or oils or petroleum stocks. Preferably, $R_4$ is a fatty aliphatic such as tallow alkyl, rapeseed alkyl, oleyl, cocoalkyl, soya alkyl and the like most preferred is cocoalkyl.

$R_5$ and $R_6$ can be the same or different and are independently selected from an aliphatic moiety of from about 1 to about 22 carbon atoms, or —$(C_aH_{2a}O)_nH$ wherein a is 2, 3, or 4 and n is from about 1 to about 20, or 2-hydroxyl-2-phenylethyl. Preferably, $R_5$ and $R_6$ are independently selected from $C_1$ to $C_3$ alkyl groups. Most preferably, both $R_5$ and $R_6$ are —$CH_3$.

Z is a bridging group of the formula —$(C_aH_{2a}O)_n$—$(CHY)_x$— wherein a is from about 1 to about 4, n is from 0 to about 10, and x is from about 1 to about 10 and Y is the same or different at each occurrence and is selected from the group consisting of hydrogen and hydroxyl groups. A particularly useful bridging group is —$CH_2CHOHCH_2$—.

$R_7$ can be chosen from amine groups having the formula —$NR_8R_9$ wherein $R_8$ and $R_9$ are the same or different and can be an aliphatic moiety of from about 1 to about 22 carbon atoms. Alternatively, $R_8$ and $R_9$ can be —$(C_aH_{2a}O)_nH$ wherein a is 2, 3, or 4 and n is from about 1 to about 20. In another embodiment, $R_8$ and/or $R_9$ can be 2-hydroxyl-2-phenylethyl.

$R_8$ and $R_9$ along with N can alternatively form a heterocyclic moiety having from about 2 to about 8 carbon atoms.

Suitable heterocyclic groups include, but are not limited to, imidazole, benzimidazole, 1,2,4-triazole, pyrrole, piperidine, and morpholine.

$R_7$ can yet alternatively be a sulfur moiety having the formula —$SR_{10}$ wherein $R_{10}$ is selected from a straight or branched chain aliphatic moiety having from 1 to about 22 carbon atoms, or phenyl, or a heterocyclic moiety containing N, S or O and having from about 2 to about 8 carbon atoms, preferably with methyl, ethyl or phenyl substitutions on the heterocyclic ring. A suitable sulfur moiety is a 2-mercaptobenzothiazole group.

When $R_7$ is an amine of the formula —$NR_8R_9$, performance of the preservative composition may be enhanced by including copper ions in the composition. In such compositions, the compound of the general formula II includes a quaternary ammonium moiety and a coordinating amine moiety linked via bridging group —Z—. The ratio of copper ions to the compound of the general formula II in the composition can range from about 100:1 to about 1:100 wt/wt, preferably from about 5:1 to about 1:2 wt/wt, most preferably from about 2.5:1 to about 1.5:1 wt/wt. Especially preferred is $R_7$ having the formula —$N(CH_2CH_2OH)_2$.

The compound of formula (II) may be made in accordance with the following method:

An amine is provided having the formula

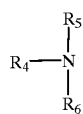

wherein $R_4$, $R_5$ and $R_6$ are as described above. The amine is then reacted with epichlorhydrin in the presence of water, preferably at a temperature of about 0° C. to about 25° C., to form an epoxy quaternary ammonium compound having the formula

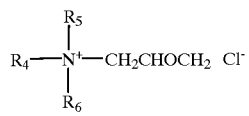

The epoxy quaternary ammonium compound is then reacted with a compound having the formula $HR_7$ in the presence of water and preferably at a temperature of from about 0° C. to about 50° C. to produce the compound of formula (II).

Examples of suitable compounds of formula (II) include:

dimethylcocoalkyl(3-(benzimidazol-1-yl)-2-hydroxypropyl)ammonium chlorides,
dimethylcocoalkyl(3-(1,2,4-triazol-1-yl)-2-hydroxypropyl)ammonium chlorides,
dimethylcocoalkyl(3-(morpholin-4-yl)-2-hydroxypropyl)ammonium chlorides,
dimethylcocoalkyl(3-(pyrazol-1-yl)-2-hydroxypropyl)ammonium chlorides,
dimethylcocoalkyl(3-(piperidin-1-yl)-2-hydroxypropyl)ammonium chlorides,
dimethylcocoalkyl(3-(benzothiazol-2-ylthio)-2-hydroxypropyl)ammonium chlorides,
dimethylcocoalkyl(3-(N-oxopyridin-2-ylthio)-2-hydroxypropyl)ammonium chlorides,
dimethylcocoalkyl(3-(4,6-dimethylpyrimidin-2-ylthio)-2-hydroxypropyl)ammonium chlorides,
dimethylcocoalkyl(3-(thiazolin-2-ylthio)-2-hydroxypropyl)ammonium chlorides,
dimethylcocoalkyl (3-(4-methyl-4H-1,2,4-triazol-3-ylthio)-2-hydroxypropyl)ammonium chlorides, and
dimethylcocoalkyl(3-(1-methylimidazol-2-ylthio)-2-hydroxypropyl)ammonium chlorides.

An example of a suitable compound of formula (II) which may be complexed with copper, for example in 2:1 proportion, is dimethylcocoalkyl(3-(2,2'-di(hydroxyethyl)amino)-2-hydroxypropyl)ammonium chlorides.

The following Examples illustrate the preparation of compounds of formula (II) and their effectiveness in preserving wood.

EXAMPLE 7

265.7 grams of epichlorhydrin and 1500 grams of water were added to a 5-liter flask and stirred together. The solution was cooled to about 5° C. and then 750.2 grams of dimethylcocoalkylamine (available from Akzo Nobel Chemicals Inc. of Chicago, Ill. under the designation Armeen DMCD) were slowly added over a thirty minute period. The solution was stirred and maintained at 5° C. for 3½ hours. Then 3000.72 grams of diethanolamine were added over a ten minute period. While stirring the solution was allowed to warm to room temperature over several hours.

The resulting sample solution contained about 38% dimethylcocoalkyl(3-(2,2'-di(hydroxyethyl)amino)-2-hydroxypropyl)ammonium chlorides product.

EXAMPLE 8

355.36 grams of basic copper carbonate was mixed with 394.76 grams of the resulting sample solution of Example 7, 575.93 grams of diethanolamine and 673.9 grams of deionized water in a 3-liter flask. The solution was cooled in an ice bath with stirring. A dark blue homogeneous liquid was obtained containing a copper complex of the dimethylcocoalkyl(3-(2,2'-di(hydroxyethyl)amino)-2-hydroxypropyl)ammonium chlorides product of Example 7.

Compounds of the formula II were evaluated against *C. puteana* fungus as described previously. The compounds tested and the results achieved are reported in Table III.

TABLE III

| COMPOUND | Trial | Growth Inhibition (*C. puteana*) |
| --- | --- | --- |
| Dimethylcocoalkyl(3-(2,2'-di(hydroxyethyl)amino)-2-hydroxypropyl)ammonium | 1 | 9 |
| 2:1 Copper complex with above compound and diethanolamine | 1 | 9 |
| Dimethylcocoalkyl(3-(benzimidazol-1-yl)-2-hydroxypropyl)ammonium chlorides | 2 | 9 |
| Dimethylcocoalkyl(3-(1,2,4-triazol-1-yl)-2-hydroxypropyl)ammonium chlorides | 1 | 8 |
| Dimethylcocoalkyl(3-(morpholin-4-yl)-2-hydroxypropyl)ammonium chlorides | 2 | 9 |
| Dimethylcocoalkyl(3-(pyrazol-1-yl)-2-hydroxypropyl)ammonium chlorides | 2 | 8 |
| Dimethylcocoalkyl(3-(piperidin-1-yl)-2-hydroxypropyl)ammonium chlorides | 2 | 9 |

TABLE III-continued

| COMPOUND | Trial | Growth Inhibition (*C. puteana*) |
|---|---|---|
| Dimethylcocoalkyl(3-(benzothiazol-2-ylthio)-2-hydroxypropyl)ammonium chlorides | 2 | 6 |
| Dimethylcocoalkyl(3-(N-oxopyridin-2-ylthio)-2-hydroxypropyl)ammonium chlorides | 2 | 6 |
| Dimethylcocoalkyl(3-(4,6-dimethylpyrimidin-2-ylthio)-2-hydroxypropyl)ammonium | 2 | 9 |
| Dimethylcocoalkyl(3-(thiazolin-2-ylthio)-2-hydroxypropyl)ammonium chlorides | 1 | 8 |
| Dimethylcocoalkyl(3-(4-methyl-4H-1,2,4-triazol-3-ylthio)-2-hydroxypropyl)ammonium | 1 | 7 |
| Dimethylcocoalkyl(3-(1-methylimidazol-2-ylthio)-2-hydroxypropyl)ammonium chlorides | 1 | 9 |
| Trimethylcocoalkylammonium chlorides (Comparative Standard) | 1 | 10 |
| Trimethylcocoalkylammonium chlorides (Comparative Standard) | 2 | 10 |

EXAMPLE 9

Compounds of the general formula II were field-tested in compositions alone and in combination with copper ions. Specifically, field studies were conducted in accordance with the methodology of the American Wood Preserves' Association (AWPA) standard E7-90. The test stakes were southern yellow pine sapwood. They were treated as 19×19×100 mm mother stakes which were cut into 19×19×45 mm daughter stakes before installation. There were ten replicates per treatment per level. A rating of 10 indicates sound, 0 is failure. The results are given in Table IV as the average of the 10 replicates.

TABLE IV

| Preservative | Target Retention | Calculated Retention | 12 months | | 24 months | | 36 month | |
|---|---|---|---|---|---|---|---|---|
| | | | Decay | Termite | Decay | Termite | Decay | Termite |
| Formula II | 0.05 | 0.05 | 8.8 | 10 | 2.3 | 6.2 | 0.7 | 2.2 |
| Compound* | 0.10 | 0.10 | 9.8 | 9.9 | 4.4 | 7.7 | — | — |
| | 0.25 | 0.26 | 9.9 | 10 | 8.2 | 9.0 | 2.9 | 7.7 |
| | 0.40 | 0.40 | 10 | 10 | 8.3 | 9.0 | 4.3 | 7.4 |
| | 0.60 | 0.63 | 10 | 10 | 9.1 | 9.3 | 7.1 | 8.0 |
| 2:1 Copper | 0.05 | 0.05 | 10 | 10 | 8.1 | 9.4 | 4.0 | 7.4 |
| Complex with | 0.10 | 0.10 | 10 | 10 | 9.5 | 9.8 | 8.5 | 9.2 |
| Form II Com- | 0.25 | 0.26 | 10 | 10 | 10 | 10 | 9.8 | 10 |
| pound and | 0.40 | 0.41 | 10 | 10 | 10 | 10 | 10 | 10 |
| ethanolamine | 0.60 | 0.62 | 10 | 10 | 10 | 10 | 10 | 10 |
| CCA Type C | 0.14 | 0.15 | 10 | 10 | 9.9 | 10 | 10 | 10 |
| (Comparative | 0.20 | 0.21 | 10 | 10 | 10 | 10 | 10 | 10 |
| Standard) | 0.28 | 0.29 | 10 | 10 | 10 | 10 | 10 | 10 |
| | 0.40 | 0.39 | 10 | 10 | 10 | 10 | 10 | 10 |
| Untreated | — | — | 6.5 | 9.5 | 1.8 | 5.5 | 0.0 | 2.1 |

*Dimethylcocoalkyl(3-(2,2'-di(hydroxyethyl)amino)-2-hydropropyl)ammonium chlorides.

As the foregoing data show, the wood preservative performance of compounds of the general formula II can be enhanced by the addition of copper ions to the wood preservative composition.

In yet another embodiment the biocidal preservative composition includes a compound having the formula (III)

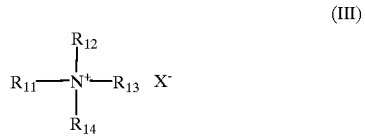

(III)

wherein $X^-$ is an anion such as, but not limited to, chloride, fluoride, bromide, iodide, acetate, methylsulfate, formate, carbonate, methylcarbonate, nitrate, nitrite, hydroxide, borate, tetraborate, perchlorate, periodate, and phosphate. Preferably, $X^-$ is a halide, most preferably chloride.

$R_{11}$, $R_{12}$ and $R_{13}$ can be the same or different and can be a straight or branched chain aliphatic moiety of from 1 to about 22 carbon atoms, preferably 10 to 20 carbon atoms, most preferably 12 to 18 carbon atoms. The aliphatic moiety may have a fixed chain length or may be of mixed chain length such as those groups derived from natural fats or oils or petroleum stocks. Preferably, the aliphatic moiety is a fatty aliphatic such as tallow alkyl, rapeseed alkyl, oleyl, cocoalkyl, soya alkyl and the like. Most preferred is cocoalkyl.

One or more of $R_{11}$, $R_{12}$, and $R_{13}$ can alternatively be a benzyl moiety that can have one or more ring substituents selected from chloro, methyl, ethyl, propyl, bromo, iodo, fluoro, trifluoromethyl, hydroxy, methoxy or phenyl.

One or two of $R_{11}$, $R_{12}$ and $R_{13}$ can alternatively be $R_{14}$. $R_{14}$ is a group having the formula —$(CH_2$—$CHR_{15}$—$O)_x$ $R_{16}$ wherein x is 1 to 20; $R_{15}$ is hydrogen, methyl, ethyl or phenyl $R_{16}$ is a benzyl, picoyl or naphthobenzyl moiety that can have ring substitutions selected from chloro, methyl, ethyl, propyl, bromo, iodo, fluoro, trifluoromethyl, hydroxy, methoxy and phenyl. Alternatively, $R_{16}$ is a group having the formula —$(CH_2)_yR_{17}$ wherein y=1 to 5 and $R_{17}$ is a moiety selected from the group consisting of nitrogen-containing heterocyclic groups having 5 to 8 members in the ring. Such groups include, for example, morpholin-4-yl, piperidin-1-yl and pyrrolidin-1-yl groups.

In particularly useful compounds of the formula (III), $R_{11}$, $R_{12}$ and $R_{13}$ are the same or different and are selected from the group consisting of straight chain $C_1$ to $C_{22}$ aliphatic moieties and $R_{14}$ is —$CH_2CH_2OR_{16}$ where $R_{16}$ is an optionally substituted benzyl moiety. In more preferred compounds, $R_{11}$ is a straight chain $C_{12}$ to $C_{18}$ aliphatic moiety, $R_{12}$ and $R_{13}$ are $C_1$ to $C_3$ alkyl moieties and $R_{14}$ is —$CH_2CH_2OR_{16}$ wherein $R_{16}$ is a 3,4-disubstituted benzyl moiety. Most preferably, in these preferred compounds $R_{12}$ and $R_{13}$ are both methyl and $R_{16}$ is a chloro- and methoxy-substituted benzyl.

A compound of formula (III) can be prepared by reacting a monoethoxylated or diethoxylated quaternary alkylammonium compound with a compound of formula $R_{16}X$, wherein X is a halide, in the presence of an alkali metal hydroxide as shown in Example 10.

EXAMPLE 10

To a 500 milliliter 3 neck round bottom flask was added 65.18 grams of a 58% monoethoxylated dimethylcocoalkylammonium chlorides in isopropyl alcohol solution, 9.80 grams of 88% potassium hydroxide pellets and 50 grams of isopropyl alcohol. The flask was fitted with an overhead stirrer and a condenser. Stirring was begun to disperse the caustic pellets. After the pellets were broken up, 30.00 grams of 3,4-dichlorobenzyl chloride was added directly to the flask. The mixture was stirred al ambient temperature for three hours, before refluxing for one hour and ten minutes. The reaction mixture was then filtered to remove solids and the excess solvent was stripped off.

There was 84.28 grams of product recovered which was assayed by quaternary titration as 63.8% active. A CMR spectra of the solution showed the desired product, dimethyl (3,4-dichlorobenzyloxyethyl)cocoalkylammonium chlorides.

EXAMPLE 11

To a 500 milliliter 3 neck round bottom flask was added 86.21 grams of a 58% monoethoxylated dimethylcocoalkylammonium chlorides in isopropyl alcohol solution and a slurry of 20.35 grams of 87.1% potassium hydroxide in 50 grams of isopropyl. The flask was fitted with an overhead stirrer and a condenser. Then 29.40 grams of 4-(2-chloroethyl)morpholine was added directly to the flask. Stirring was begun and the reaction mixture was refluxed for 5¾ hours. The reaction mixture was then filtered to remove solids and the excess solvent was stripped off.

A CMR spectra of the solution showed the desired product, dimethyl(5-(morpholin-4-yl)ethyloxyethyl) cocoalkylammonium chlorides, was formed with only a trace of the unreacted ethoxylated quaternary.

EXAMPLE 12

Five hundred twenty six grams of a 60% monoethoxylated dimethylcocoalkylammonium chlorides in isopropyl alcohol solution and 67.4 grams of potassium hydroxide are added to a three-neck two liter round bottom flask which was fitted with a reflux condenser, a mechanical overhead stirrer, and a nitrogen inlet. The flask was placed in an oil bath which was heated to 90° C. while the slurry stirred under nitrogen. The 224 grams of 3,4-dimethoxybenzyl chloride was added in 40 gram increments over one hour. The solution stirred at reflux conditions for a total of 16.5 hours. After cooling to ambient temperature, the solution was filtered and placed back in the reaction flask along with 13.5 grams of potassium hydroxide. The solution was heated to reflux. After reaching reflux, an additional 44.8 grams of 3,4-dimethoxybenzyl chloride was added. The solution was stirred for 4.5 hours, cooled to ambient temperature, and filtered. The solids was rinsed with a small amount of isopropyl alcohol which was added to the reaction product. The identity of the product, dimethyl(3,4-dimethoxybenzyl-oxyethyl)cocoalkylammonium chlorides, was confirmed by $^{13}C$ NMR.

The most preferred compound is the 3,4-dichlorobenzyl ether derivative of a monoethoxylated dimethylalkylammonium compound, which is preferably prepared from monoethoxylated dimethylcocoalkylammonium chlorides and 3,4-dichlorobenzyl chloride.

Other suitable compounds of formula (III) include the following derivatives of the monoethoxylated dimethylcocoalkylammonium chlorides:

2-morpholin-4-ylethyl ether,
2-piperidin-1-ylethyl ether,
2-pyrrolidin-1-ylethyl ether,
4-methylbenzyl ether,
3-methoxybenzyl ether,
4-chlorobenzyl ether,
2-picolyl ether,
3-picolyl ether,
4-picolyl ether,
2,6-dichlorobenzyl ether,
2,4-dichlorobenzyl ether,
3,4-difluorobenzyl ether,
3-iodobenzyl ether,
4-iodobenzyl ether,
4-fluorobenzyl ether,
2-methyl-1-naphthobenzyl ether, and
1-naphthobenzyl ether.

Also suitable are the following derivatives of diethoxylated methylcocoalkylammonium chloride:

bis(2-picolyl ether),
bis(4-picolyl ether),
bis(2-pyrrolidin-1ylethyl ether),
bis(2-piperidin-1-ylethyl ether),
bis(2-morpholin-4-ylethyl ether),
bis(3-pyrrolidin-1-ylpropyl ether),
bis(2-(1-methyl)pyrollidin-2-ylethyl ether),
bis(4-methylbenzyl ether),
bis(3-methoxybenzyl ether), and
bis(3,4-dichlorobenzyl ether).

Compounds of the formula III were evaluated against *C. puteana* fungus as described previously. The compounds tested and the results achieved are reported in Table V.

TABLE V

| Cationic Compound | Trial | Growth Inhibition (*C. puteana*) |
| --- | --- | --- |
| Monoethoxylated dimethyl-cocoalkyl | | |
| Benzyl ether | 11 | 10 |
| 2-Methylbenzyl ether | 5 | 9 |
| 4-Methylbenzyl ether | 9 | 9 |
| 2,5-Dimethylbenzyl ether | 6 | 8 |
| 3,4-Dimethylbenzyl ether | 6 | 9 |
| 2,4,6-Trimethylbenzyl ether | 6 | 8 |
| 4-(tert-Butyl)benzyl ether | 6 | 8 |
| 1-Naphthobenzyl ether | 4 | 5 |
| 2-Methyl-1-naphthobenzyl ether | 4 | 9 |
| 2-Naphthobenzyl ether | 10 | 9 |
| 3-Methoxybenzyl ether | 9 | 8 |
| 3,4-Dimethoxybenzyl ether | 11 | 10 |
| 3,5-Dimethoxybenzyl ether | 6 | 8 |
| 4-Fluorobenzyl ether | 4 | 7 |
| 3,4-Difluorobenzyl ether | 3 | 9 |
| 2-Chlorobenzyl ether | 10 | 8 |
| 4-Chlorobenzyl ether | 3 | 8 |
| 2,3-Dichlorobenzyl ether | 11 | 8 |

TABLE V-continued

| Cationic Compound | Trial | Growth Inhibition (C. puteana) |
|---|---|---|
| 2,4-Dichlorobenzyl ether | 3 | 8 |
| 2,6-Dichlorobenzyl ether | 3 | 8 |
| 3,4-Dichlorobenzyl ether | 2/7 | 10/10 |
| 2-Iodobenzyl ether | 6 | 8 |
| 3-Iodobenzyl ether | 4 | 8 |
| 4-Iodobenzyl ether | 4 | 9 |
| 2-Morpholin-4-ylethyl ether | 9 | 9 |
| 2-Piperidin-1-ylethyl ether | 9 | 9 |
| 2-Pyrrolidin-1-ylethyl ether | 9 | 9 |
| 2-Picolyl ether | 3 | 8 |
| 3-Picolyl ether | 3 | 9 |
| 4-Picolyl ether | 3 | 9 |
| Diethoxylated methyl-cocoalkyl | | |
| Bis(4-methylbenzyl ether) | 1 | 7 |
| Bis(3-methoxybenzyl ether) | 2 | 8 |
| Bis(3,4-dichlorobenzyl ether) | 2/3 | 4/10 |
| Bis(2-picolyl ether) | 8 | 7 |
| Bis(4-picolyl ether) | 8 | 7 |
| Bis(2-morpholin-4-ylethyl ether) | 8 | 8 |
| Bis(2-piperidin-1-ylethyl ether) | 8 | 7 |
| Bis(2-pyrrolidin-1-ylethyl ether) | 8 | 9 |
| Bis(3-pyrrolidin-1-ylpropyl ether) | 8 | 7 |
| Bis(2-(1-methyl)pyrollidin-2-yl)ethyl | 8 | 6 |
| Monoethoxylated methyl-dicocoalkyl | | |
| Benzyl ether | 11 | 5 |
| Trimethylcocoalkylammonium | | |
| (Comparative Standard) | 1 | 10 |
|  | 2 | 10 |
|  | 3 | 10 |
|  | 4 | 10 |
|  | 5 | 10 |
|  | 6 | 9 |
|  | 7 | 9 |
|  | 8 | 9 |
|  | 9 | 10 |
|  | 10 | 8 |
|  | 11 | 10 |

Biocidal preservative compositions can also include other components to enhance the function of the biocide. For example, compositions including the biocidal agents described hereinabove generally also include a liquid carrier. Such carriers include one or more solvents for the biocidal agent. Such solvents can be, for example, a mixture in water of an ether of an alkanol and a diol (e.g., diethylene glycol monomethyl ether, diethylene glycol diethyl ether, propylene glycol monomethyl ether, dipropylene glycol monomethyl ether), and/or a monocarboxylic acid (e.g., formic acid, acetic acid, propionic acid), and/or a saturated aliphatic diol containing from 2 to 10 carbon atoms (e.g., ethylene glycol, diethylene glycol, propylene glycols, butylene glycols, hexalene glycols). Preferably, however, the solvent is simply water. The relative proportions of the components of the solvent can be varied over a wide range. Preferred compositions include from about 0.01 to about 50% by weight of biocide, more preferably from about 0.1% to about 10% biocide. The liquid carrier can also include an oil such as vegetable oil, linseed oil, soya oil, pine oil, tall oil, or mineral oil.

The liquid carrier can optionally also include a fixative to facilitate the binding of the biocide to the treated material such as wood. Such fixative agents include starch, carboxymethyl cellulose, gum arabic, polyvinyl alcohol, colophony or colophony esters, humic acid, glycerophthalic resins, and various other resins.

The wood preservative composition can also include a water repellant. Suitable water repellants include either water soluble or emulsifiable versions of the following: silicones, fatty acid salts (such as, for example, calcium, magnesium or aluminum stearate), polyurethanes, alkyl biphenyls, fatty alcohols, hydrocarbon waxes, phosphated glycerides, PVP copolymers, and ethylene and propylene homopolymers.

While the preservatives described above exhibit biocidal properties with respect to microorganisms such as molds and fungus, other biocides (e.g., insecticides) can also be included in the preservative composition. Suitable insecticides for use in wood preservatives are those having a biocidal effect on xylophagous insects such as, for example, termites, wood eating ants, Capricorn beetles, deathwatch beetles, powder post beetles, and like insects. Exemplary insecticides include DDT (dichlorodiphenyltrichloroethane), methoxychlor (2,2'-bis(4-methoxyphenyl)-1,1,1-trichloroethane), lindane (gamma isomer of hexachloro-cyclohexane), chlordane (octachlorohexahydromethanoindene), aldrin (endo hexachlorohexahydrodimethanonaphthalene), toxaphene, ethion (O,O,O',O'-tetraethyl-S,S'-methylenedithiophoshate), parathion (O,O-diethyl-O-paranitrophenyl thiophosphate), phosalone (O,O-diethyl-3-dithiophosporyl-methyl-6-chlorobenzoxazolone), sevin (1-naphtyl N-methylcarbamate), carbofuran (dimethyldihydrobenzofuryl N-methylcarbamate), decamethrin (alpha-cyanophenoxybenzyldibromovinyl-dimethylcyclopropane-carboxylate), cypermethrin (phenoxybenzyl cis-transdimethyldichlorovinylcyclopropane-carboxylate), and fenvalerate (alpha-cyanophenoxybenzyl chlorphenyl-methylbutylbutyrate), for example.

The biocidal preservatives described herein can be applied by brushing, spraying, soaking, and similar treatments. Freshly milled timber and wood for millwork or joinery are preferably treated with preservatives by dipping and double vacuum treatments. Pressure treatment is preferably employed to treat wood used in the ground and in many above ground applications.

While the above description contains many specifics, these specifics should not be construed as limiting, but merely as exemplifications of preferred embodiments thereof. Those skilled in the art will envision many other possible variations that are within the scope and spirit of the invention as defined by the claim appended hereto.

What is claimed is:

1. A method for preserving wood comprising the steps of:
providing a wood preservative composition by mixing a liquid carrier with a compound of the formula:

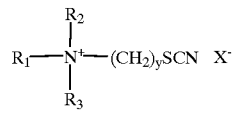

wherein $X^-$ is an anion, y is from 1 to about 12 and $R_1$, $R_2$ and $R_3$ can be the same or different and are independently selected from the group consisting of a straight or branched chain aliphatic moiety of from about 1 to about 22 carbon atoms, a benzyl moiety with or without substituents, $-(C_aH_{2a}O)_nH$ wherein a is 2, 3, or 4 and n is from about 1 to about 20, 2-hydroxyl-2-phenylethyl, $R_1$ and $R_2$ with $N^+$ optionally forming a heterocyclic moiety having from about 4 to about 10 carbon atoms: and applying said wood preservative composition to wood.

2. A method as in claim 1 wherein in the compound of the formula

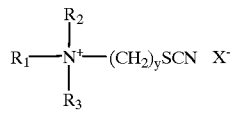

$R_1$, $R_2$ and $R_3$ can be the same or different and are independently selected from the group consisting of aliphatic moieties of from 1 to about 22 carbon atoms.

3. A method as in claim 2 wherein y is from 1 to about 3, $R_1$ is a straight chain aliphatic moiety of from about 10 to about 18 carbon atoms and $R_2$ and $R_3$ can be the same or different and are independently selected from alkyl groups having from 1 to 3 carbon atoms.

4. A method as in claim 3 wherein y is from 1 to 12 and $R_2$ and $R_3$ are both —$CH_3$.

5. The method of claim 1 wherein the wood preservative composition further includes an insecticide.

6. The method of claim 1 wherein the wood preservative composition further includes a water repellant.

7. A method for preserving wood comprising the steps of:
   providing a wood preservative composition by mixing a liquid carrier with a compound selected from the group consisting of dimethyldodecylthiocyanatomethylammonium chloride and dimethylcocothiocyanatomethylammonium chlorides; and
   applying said wood preservative composition to wood.

8. A biocidal composition comprising a carrier, a water repellant and a biocidally effective amount of a compound of the formula

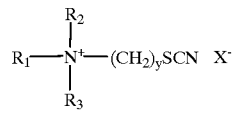

wherein $X^-$ is an anion, y is from about 1 to about 12, and $R_1$, $R_2$ and $R_3$ can be the same or different and are independently selected from the group consisting of a straight or branched chain aliphatic moiety of from about 1 to about 22 carbon atoms, a benzyl moiety with or without substituents, —$(C_2H_{2a}O)_nH$ wherein a is 2, 3 or 4 and n is from about 1 to about 20 and 2-hydroxyl-2-phenylethyl, $R_1$ and $R_2$ with $N^+$ optionally forming a heterocyclic moiety having from about 4 to about 10 carbon atoms.

9. A biocidal composition comprising a carrier, an insecticide and a biocidally effective amount of a compound of the formula

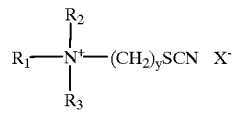

wherein $X^-$ is an anion, y is from about 1 to about 12, and $R_1$, $R_2$ and $R_3$ can be the same or different and are independently selected from the group consisting of a straight or branched chain aliphatic moiety of from about 1 to about 22 carbon atoms, a benzyl moiety with or without substituents, —$(C_2H_{2a}O)_nH$ wherein a is 2, 3 or 4 and n is from about 1 to about 20 and 2-hydroxyl-2-phenylethyl, $R_1$ and $R_2$ with $N^+$ optionally forming a heterocyclic moiety having from about 4 to about 10 carbon atoms.

* * * * *

UNITED STATES PATENT AND TRADEMARK OFFICE
Certificate

Patent No. 6,172,117                                                                                        Patented: January 9, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: John P. Bell, Ossining, New York; Andress Doyle, Pleasantville, New York; and Stanley B. Mirviss, Stamford, Connecticut.

Signed and Sealed this Seventh Day of January 2003.

<div align="right">

JOSE' G. DEES
*Supervisory Patent Examiner*
Art Unit 1616

</div>